US010023151B2

(12) United States Patent
Samadani et al.

(10) Patent No.: US 10,023,151 B2
(45) Date of Patent: Jul. 17, 2018

(54) AUTONOMOUS VEHICLE SECURITY

(71) Applicant: QUALCOMM Incorporated, San Diego, CA (US)

(72) Inventors: Ramin Samadani, Menlo Park, CA (US); Mastooreh Salajegheh, Santa Clara, CA (US); Hui Chao, San Jose, CA (US)

(73) Assignee: QUALCOMM Incorporated, San Diego, CA (US)

( * ) Notice: Subject to any disclaimer, the term of this patent is extended or adjusted under 35 U.S.C. 154(b) by 0 days.

(21) Appl. No.: 15/262,451

(22) Filed: Sep. 12, 2016

(65) Prior Publication Data
US 2018/0072265 A1   Mar. 15, 2018

(51) Int. Cl.
| | |
|---|---|
| *G05B 19/00* | (2006.01) |
| *B60R 25/24* | (2013.01) |
| *G08G 1/00* | (2006.01) |
| *G08B 21/18* | (2006.01) |
| *H04L 29/08* | (2006.01) |

(52) U.S. Cl.
CPC .......... *B60R 25/24* (2013.01); *G08B 21/182* (2013.01); *G08G 1/20* (2013.01); *H04L 67/12* (2013.01)

(58) Field of Classification Search
CPC ......... G08B 21/182; B60R 25/04; G08G 1/00
USPC ..... 701/23; 340/5.1, 5.2, 5.21, 5.3, 5.8, 5.82
See application file for complete search history.

(56) References Cited

U.S. PATENT DOCUMENTS

| | | | | |
|---|---|---|---|---|
| 6,249,227 | B1* | 6/2001 | Brady ............... | G06K 19/0723 340/572.1 |
| 6,493,614 | B1* | 12/2002 | Jung .................. | G05D 1/0246 180/168 |
| 6,720,866 | B1* | 4/2004 | Sorrells ............. | G06K 19/0717 340/10.34 |
| 7,149,658 | B2* | 12/2006 | Kadaba ............. | G06K 19/0717 702/184 |
| 8,150,633 | B2* | 4/2012 | Burke ................ | A22C 29/005 324/668 |
| 8,849,494 | B1* | 9/2014 | Herbach ............ | B60W 30/00 701/24 |
| 9,283,960 | B1* | 3/2016 | Lavoie .............. | B60W 30/06 |
| 9,463,793 | B2* | 10/2016 | Lind .................. | B60W 30/00 |
| 9,477,938 | B1* | 10/2016 | Russell ............. | G06Q 10/087 |
| 9,658,620 | B1* | 5/2017 | Urmson ............. | G05D 1/0088 |
| 2004/0100379 | A1* | 5/2004 | Boman .............. | G06Q 10/047 340/539.26 |
| 2005/0073406 | A1* | 4/2005 | Easley ............... | G06Q 10/08 340/539.1 |
| 2012/0083960 | A1 | 4/2012 | Zhu et al. | |

(Continued)

FOREIGN PATENT DOCUMENTS

WO    2015099679 A1    7/2015

*Primary Examiner* — Carlos E Garcia
(74) *Attorney, Agent, or Firm* — The Marbury Law Group/Qualcomm

(57) ABSTRACT

Various implementations include unmanned autonomous vehicles (UAVs) and methods for providing security for a UAV. In various implementations, a processor of the UAV may receive sensor data from a plurality of UAV sensors about an object in contact with the UAV. The processor may determine an authorization threshold based on the received sensor data. The processor may determine whether the object is authorized based on the received sensor data and the determined authorization threshold.

30 Claims, 4 Drawing Sheets

(56) References Cited

U.S. PATENT DOCUMENTS

| | | |
|---|---|---|
| 2014/0279596 A1 | 9/2014 | Waris et al. |
| 2015/0226146 A1 | 8/2015 | Elwart et al. |
| 2015/0232064 A1 | 8/2015 | Cudak et al. |
| 2017/0080900 A1* | 3/2017 | Huennekens ........... B60R 25/31 |
| 2018/0016027 A1* | 1/2018 | Cheatham, III ....... B64D 45/00 |

* cited by examiner

AUTONOMOUS VEHICLE SECURITY

BACKGROUND

Autonomous vehicles are vehicles capable of sensing their environment in navigating without a human operator. Autonomous vehicles can detect information about their location and surroundings (for example, using radar, lidar, GPS, file odometers, accelerometers, cameras, and other similar devices), and may include control systems to interpret sensory information and to identify navigation paths. Increasingly, autonomous vehicles are used to transport people and to convey goods.

However, autonomous vehicles may be more vulnerable to certain security risks because autonomous vehicles may be unable to assess certain threats and take appropriate actions. For example, an autonomous vehicle may be compromised to transport contraband or stolen goods. As another example, an autonomous vehicle might be used to deliver an explosive or other hazardous material.

SUMMARY

Various embodiments and implementations include methods implemented on an unmanned autonomous vehicle (UAV) for providing security for the UAV. Various embodiments and implementations may include receiving sensor data from a plurality of UAV sensors about an object in contact with the UAV, determining an authorization threshold based on the received sensor data, and determining whether the object is authorized based on the received sensor data and the determined authorization threshold.

In some implementations, determining the authorization threshold based on the received sensor data may include determining whether the object is a recognized object, and determining the authorization threshold based on whether the object is a recognized object. In some implementations, determining the authorization threshold based on the received sensor data may include determining whether the object is a previously authorized object, and determining the authorization threshold based on whether the object is a previously authorized object.

In some implementations, determining the authorization threshold based on the received sensor data may include determining whether a person in the UAV is a known person, and determining the authorization threshold based on whether the person in the UAV is a known person. In some implementations, determining the authorization threshold based on the received sensor data may include determining whether a person in the UAV is an alive, willing, and conscious person, and determining the authorization threshold based on whether the person in the UAV is an alive, willing, and conscious person.

In some implementations, determining the authorization threshold based on the received sensor data may include determining whether a person in the UAV is in an unusual position, and determining the authorization threshold based on whether the person in the UAV is in an unusual position. In some implementations, determining the authorization threshold based on the received sensor data may include determining whether the UAV is traveling a known path, and determining the authorization threshold based on whether the UAV is traveling the known path. In some implementations, determining the authorization threshold based on the received sensor data may include determining whether the UAV deviates from a path, and determining the authorization threshold based on whether the UAV deviates from the path.

Some implementations may further include storing information about the object in response to determining that the object is authorized. Some implementations may further include generating an indication that the object is unauthorized in response to determining that the object is not authorized. Some implementations may further include determining an action to perform when the object is not authorized, and performing the determined action. Some implementations may further include determining whether an authorization of an unauthorized object is received, and determining the action to perform in response to determining that authorization of the unauthorized object is not received.

Further embodiments include a UAV including a plurality of sensors and a processor coupled to the plurality of sensors and configured with processor-executable instructions to perform operations of the embodiment methods summarized above. Further embodiments include a non-transitory processor-readable storage medium having stored thereon processor-executable software instructions configured to cause a processor to perform operations of the embodiment methods summarized above. Further embodiments include a UAV that includes means for performing functions of the embodiment methods summarized above.

BRIEF DESCRIPTION OF THE DRAWINGS

The accompanying drawings, which are incorporated herein and constitute part of this specification, illustrate exemplary aspects, and together with the general description given above and the detailed description given below, serve to explain the features of the various aspects.

DETAILED DESCRIPTION

Figure 1A:
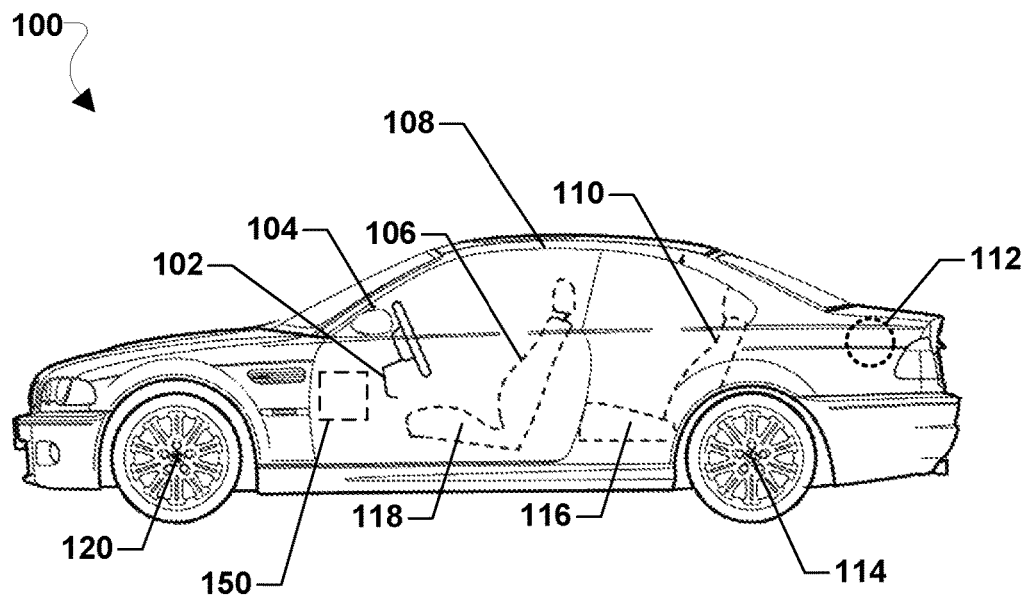
FIGS. 1A and 1B are component block diagrams illustrating a UAV suitable for implementing various implementations.

Various aspects will be described in detail with reference to the accompanying drawings. Wherever possible, the same reference numbers will be used throughout the drawings to refer to the same or like parts. References made to particular examples and implementations are for illustrative purposes, and are not intended to limit the scope of the various aspects or the claims.

Various embodiments and implementations include methods and systems that implement the methods of providing security for a UAV. Various implementations may improve the operation of a UAV by providing security to the UAV related to the detection and evaluation of objects that may be placed in or on the UAV.

As used herein, the term "UAV" refers to one of various types of unmanned autonomous vehicle. Any of a variety of vehicles may be configured to operate autonomously and work with the various implementations, including aerial vehicles, land vehicles, waterborne vehicles, and space vehicles. Various implementations are illustrated with reference to an unmanned aerial vehicle as an example of a type of UAV that may benefit from magnetic field navigation. A UAV may include an onboard computing device configured to operate the UAV without remote operating instructions (i.e., autonomously), such as from a human operator or remote computing device. Alternatively, the onboard computing device may be configured to maneuver and/or operate the UAV with some remote operating instruction or updates to instructions stored in a memory of the onboard computing device.

The terms "component," "system," "unit," and the like include a computer-related entity, such as, but not limited to, hardware, firmware, a combination of hardware and software, software, or software in execution, which are configured to perform particular operations or functions. For example, a component may be, but is not limited to, a process running on a processor, a processor, an object, an executable, a thread of execution, a program, and/or a computer. By way of illustration, both an application running on a communication device and the communication device may be referred to as a component. One or more components may reside within a process and/or thread of execution and a component may be localized on one processor or core and/or distributed between two or more processors or cores. In addition, these components may execute from various non-transitory computer readable media having various instructions and/or data structures stored thereon. Components may communicate by way of local and/or remote processes, function or procedure calls, electronic signals, data packets, memory read/writes, and other known computer, processor, and/or process related communication methodologies.

UAVs are increasingly used to transport people and to convey goods. UAVs may be more vulnerable to certain security risks because of their general inability to assess certain threats and take appropriate action. For example, a UAV may be used to transport contraband or stolen goods as well as hazardous materials of nearly any type. However, not all goods are undesirable, and UAVs may be used to convey legitimate or desired goods, including luggage, bookbags, backpacks, sports gear, music equipment, and other similar goods. Further, the desired goods may belong to a vehicle owner, or the owner's family or friends.

Various implementations provide systems and methods of providing security for UAV. In some implementations, a processor of the UAV may receive sensor data from a plurality of UAV sensors of an object in contact with the UAV. The object may be in the UAV, on the UAV, under the UAV, attached to the UAV, in a cargo area or passenger area of the UAV, or otherwise detectable or able to be sensed by a sensor of the UAV. In some implementations, the processor of the UAV may determine an authorization threshold for the object based on the received sensor data. The processor of the UAV may determine whether the object is authorized based on the received sensor data and the determined authorization threshold.

In various implementations, the processor of the UAV may determine the authorization threshold based on one or more criteria. For example, based on one or more determinations based on the received sensor data, the processor of the UAV may determine (for example, calculate, increase, or decrease) the authorization threshold. In some implementations, the processor of the UAV may determine whether the object is a recognized object, such as an object that the processor has previously detected, or which previously has been in contact with the UAV. In some implementations, the processor of the UAV may determine whether the object is previously authorized.

In some implementations, the processor of the UAV may determine whether a person in the UAV is known to the processor of the UAV. In some implementations, the processor of the UAV may determine whether the detected person is alive, willing, and/or conscious. In some implementations, the processor of the UAV may determine whether a person is in an unusual position or location in or on the UAV.

In some implementations, the processor of the UAV may determine whether the UAV is traveling a known path. In some implementations, the processor of the UAV may determine whether the UAV deviates from the known path.

Based on one or more determinations based on the received sensor data, the processor of the UAV may determine the authorization threshold.

In some implementations, in response to determining that the object is authorized, the processor of the UAV may store information about the authorized object in a memory of the UAV.

In some implementations, in response to determining that the object is not authorized, the processor of the UAV may determine an action to perform, and may perform the determined action. In some implementations, in response to determining that the object is not authorized, the processor of the UAV may generate an indication that the object is unauthorized. In some implementations, the processor of the UAV may also determine whether an authorization of the object is received (for example, in response to the indication that the object is unauthorized).

In response to determining that the authorization of the object is received, the processor of the UAV may store information about the authorized object in a memory of the UAV. In response to determining that the authorization of the object is not received, the processor of the UAV may determine the action to perform.

Figure 1B:
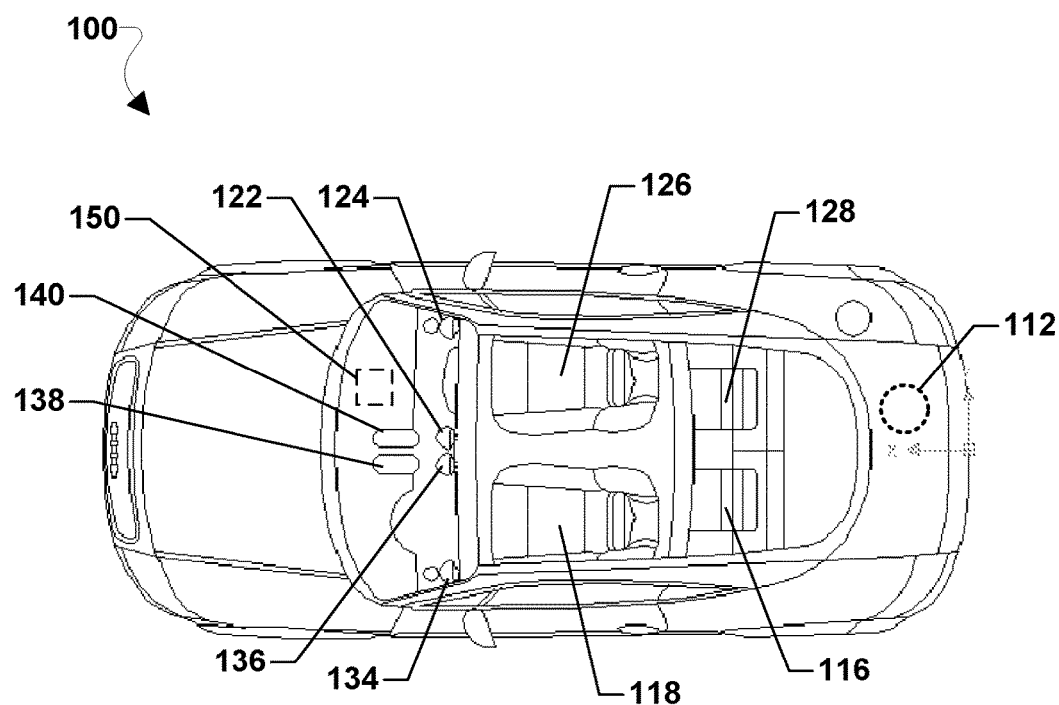

Various implementations may be implemented within a variety of UAVs, an example UAV 100 of which is illustrated in FIGS. 1A and 1B. With reference to FIGS. 1A and 1B, the UAV 100 may include a plurality of sensors 102-140 disposed in or on the UAV. Each of the sensors 102-140 may be in wired or wireless communication with a processor 150, as well as with each other. The sensors 102-140 may include one or more of a wide variety of sensors capable of detecting a variety of information, such as cameras (e.g., 122, 136), optical sensors, photo optic sensors, pressure sensors (e.g., 114, 120), humidity sensors, temperature sensors (e.g., 102), position sensors (e.g., 108), acceleration sensors (e.g., 138), vibration sensors, gyroscopes (e.g., 140), gravimeters, impact sensors (e.g., 150), force meters, stress meters, strain sensors, fluid sensors, chemical sensors, gas content analyzers, pH sensors, radiation sensors, Geiger counters, neutron detectors, biological material sensors, radar (e.g., 104), lidar, IR sensors, ultrasonic sensors, microphones (e.g., 124, 134), occupancy sensors (e.g., 112, 116, 118, 126, 128), proximity sensors, motion sensors, and other sensors. The sensors 102-140 may provide sensor data to the processor 150. In various embodiments, the sensors 102-140 may provide a variety of sensor data regarding objects and people in an on the UAV to the processor 150.

Figure 2:
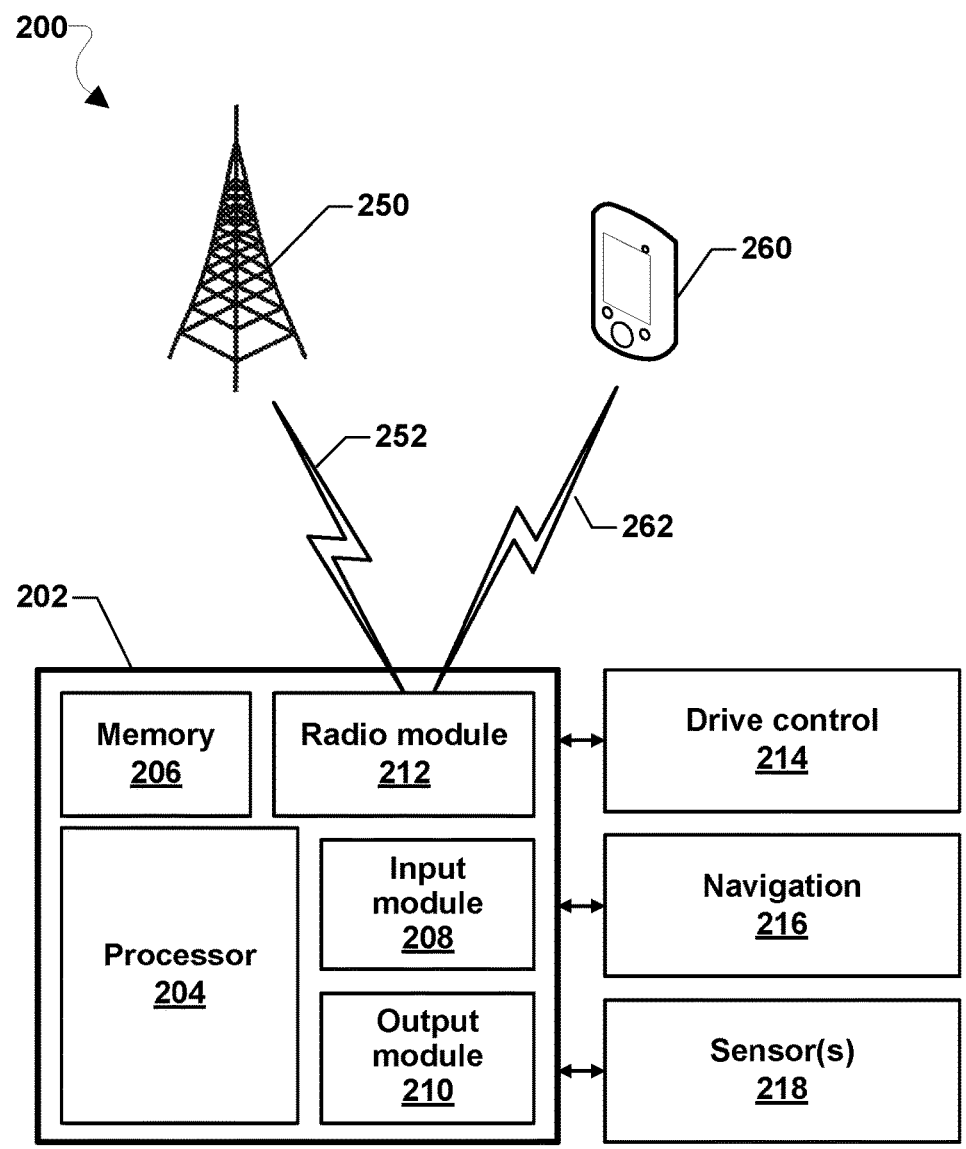
FIG. 2 is a component block diagram illustrating components of a UAV suitable for implementing various implementations.

FIG. 2 is a component block diagram illustrating components 200 of the UAV 100 (e.g., FIG. 1) according to various implementations. With reference to FIGS. 1A, 1B, and 2, the components 200 may include a control unit 202, which may include various circuits and devices used to control the operation of the UAV 100. The components 200 may also include drive control components 214, navigation components 216, and one or more sensors 218.

The control unit 202 may include a processor 204 (which may be similar to the processor 150) configured with processor-executable instructions to control maneuvering, navigation, and other operations of the UAV 100, including operations of various implementations. The processor 204 may communicate with a memory 206. The control unit 202 may include an input module 208, an output module 210, and a radio module 212.

The radio module 212 may be configured for wireless communication. The radio module 212 may exchange signals 252 (e.g., command signals for controlling maneuvering, signals from navigation facilities, etc.) with a network transceiver 250, and may provide the signals 252 to the processor 204 and/or the navigation unit 216. In some implementations, the radio module 212 may enable the UAV 100 to communicate with a wireless communication device 260 through a wireless communication link 262. The wireless communication link 262 may be a bidirectional or unidirectional communication link, and may use one or more communication protocols.

The input module 208 may receive sensor data from one or more UAV sensors 218 as well as electronic signals from other components, including the drive control components 214 and the navigation components 216. The output module 210 may be used to communicate with or activate components, including the drive control components 214, the navigation components 216, and the sensor(s) 218.

The control unit 202 may be coupled to the drive control components 214 to control physical elements (for example, an engine, motors, throttles, steering elements, flight control elements, braking or deceleration elements, and the like) of the UAV 100 related to maneuvering and navigation of the UAV. The drive control components 214 may also include components that may control other devices of the UAV, including environmental controls (e.g., air conditioning and heating), external and/or interior lighting, interior and/or exterior informational displays (which may include a display screen or other devices to display information), and other similar devices.

The control unit 202 may be coupled to the navigation components 216, and may receive data from the navigation components 216 and use such data in order to determine the present position and orientation of the UAV 100, as well as an appropriate course toward a destination. In various implementations, the navigation components 216 may include a global navigation satellite system (GNSS) receiver system (e.g., one or more Global Positioning System (GPS) receivers) enabling the UAV 100 to navigate using GNSS signals. Alternatively or in addition, the navigation components 216 may include radio navigation receivers for receiving navigation beacons or other signals from radio nodes, such as navigation beacons (e.g., very high frequency (VHF) Omni Directional Radio Range (VOR) beacons), Wi-Fi access points, cellular network sites, radio station, remote computing devices, other UAVs, etc. Through control of the drive control elements 214, the processor 204 may control the UAV 100 to navigate and maneuver. The processor 204 and/or the navigation components 216 may be configured to communicate with a server through a wireless connection (e.g., a cellular data network) to receive commands to control maneuvering, receive data useful in navigation, provide real-time position reports, and assess other data.

The control unit 202 may be coupled to one or more sensors 218. The sensor(s) 218 may be similar to the sensors 102-140, and may provide a variety of data to the processor 204.

While various components 200 are illustrated or described as separate components, some or all of the components (e.g., the processor 204, the memory 206, the input module 208, the output module 210, and the radio module 212) may be integrated together in a single device or module, such as a system-on-chip module.

Figure 3:
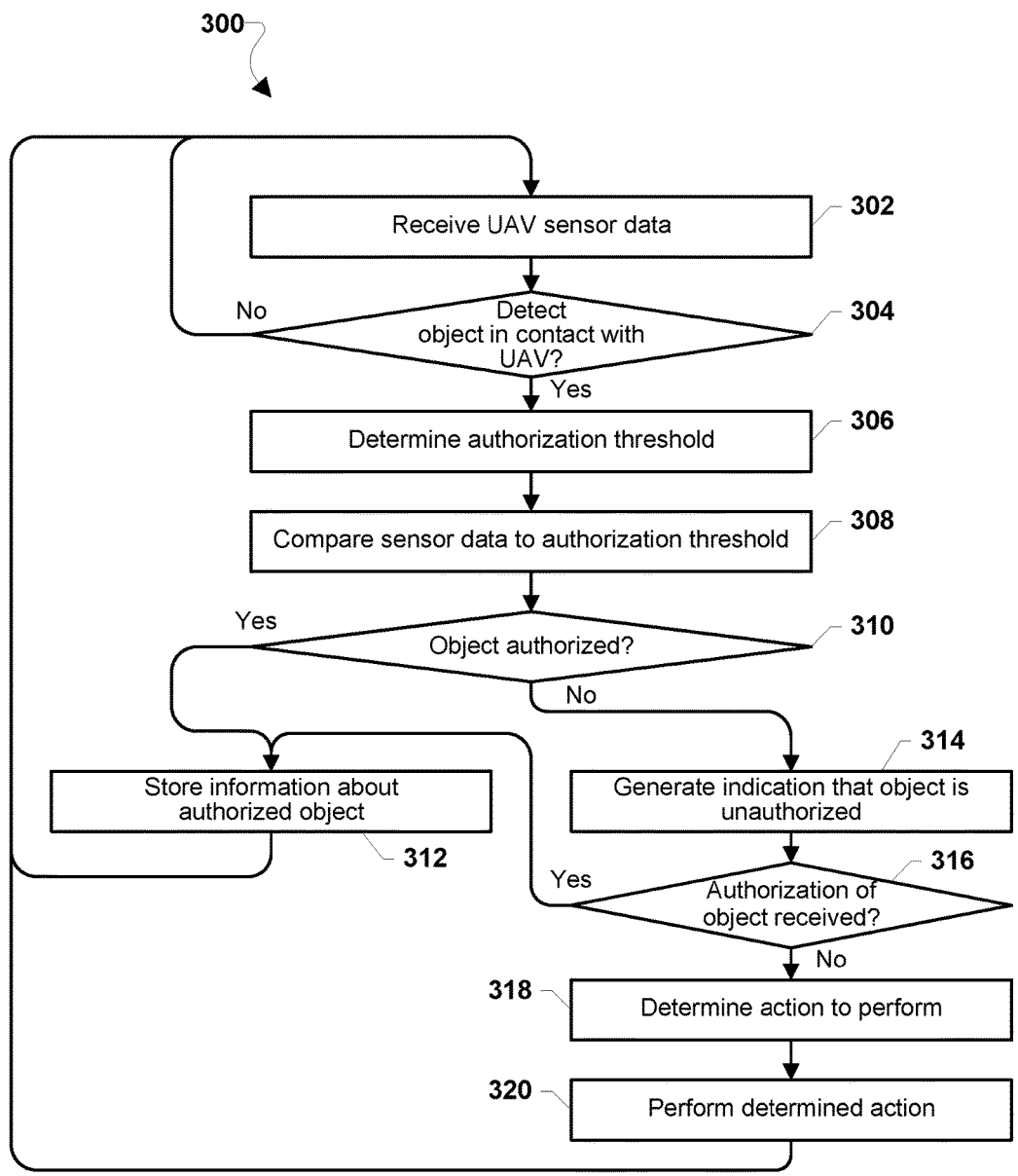
FIG. 3 is a process flow diagram illustrating an implementation method of providing security for an unmanned autonomous vehicle (UAV)

FIG. 3 illustrates a method 300 of providing security for a UAV according to some implementations. With reference to FIGS. 1-3, the method 300 may be implemented by a UAV (e.g., the UAV 100), such as under the control of a processor (e.g., the processor 204) of the UAV.

In block 302, the processor may receive sensor data from UAV sensors. In some implementations, the sensor data may be about an object in contact with the UAV. The sensors may include, for example, any or all of the sensors 102-140 and 218.

In determination block 304, the processor may determine whether the processor detects an object in contact with the UAV. The object may be in the UAV, on the UAV, under the UAV, attached to the UAV, in a cargo area or of the UAV, or otherwise detectable or sensible by a sensor of the UAV.

In some implementations, the processor may determine whether the processor detects the object in contact with the UAV based on the received sensor data. For example, the sensor data may indicate additional weight imparted by the presence of the object in or on the UAV. The sensor data may also indicate the existence of the object or the cargo area of the UAV. The sensor data may also indicate an attachment of the object to, for example, a cargo carrier, a trailer hitch, and elements of the UAV adapted to carry an object, an attachment point of the UAV, or another element of the UAV. Sensor data indicating the presence of the object may include a wide array of different types of data, such as sensors 102-140 may provide to the processor.

In response to determining that the processor does not detect an object in contact with the UAV (i.e., determination block 304="No"), the processor may again receive UAV sensor data in block 302.

In response to determining that the processor detects an object in contact with the UAV (i.e., determination block 304="Yes"), the processor may determine an authorization threshold in block 306. In various implementations, the processor may determine the authorization threshold based on one or more criteria. For example, based on one or more determinations based on the received sensor data, the processor of the UAV may calculate the authorization threshold. In some implementations, the processor may use a default or baseline authorization threshold. In some implementations, the processor may raise or lower the baseline authorization threshold based on one or more determinations using the received sensor data.

In block 308, the processor may compare the sensor data to the authorization threshold.

In determination block 310, the processor may determine whether the object is authorized. In various embodiments, the processor may determine whether the object is authorized based on the comparison of the sensor data to the authorization threshold.

In response to determining that the object is authorized (i.e., determination block 310="Yes"), the processor may store information about the authorized object in block 312. In some implementations, the processor may store the information about the authorized object in a memory of the UAV, such as the memory 206. The information may be stored in a data structure, such as database or another similar data structure. In some implementations, the stored information may include an object identifier. In some implementations, the stored information may include an authorization level associated with the authorized object. The processor may then receive UAV sensor data in block 302

In response to determining that the object is not authorized (i.e., determination block 310="No"), the processor may generate an indication that the object is unauthorized in block 314. For example, the processor may generate an indication that an unauthorized object has been detected. In some implementations, the processor may present the indication using a visual indicator, an audible indicator, a tactile indicator, or another such indicator. In some implementations, the processor may transmit the indication to, for example, a communication network (for example, via the network transceiver 250, or to a wireless communication device (for example, the wireless communication device 260 (for example, via the radio module 212).

In some implementations, the processor may provide an opportunity for authorization of an unauthorized object. For example, the processor may present a query (such as a visual query or an audible query) requesting an indication of whether the detected object is authorized. In some implementations, the query may be presented inside the UAV. In some implementations, the query may be presented outside the UAV (for example, a siren, an alarm, flashing lights, an indication on a display, or another indication). In some implementations, the processor may transmit the query to, for example, the communication network or the wireless communication device. In some implementations, the processor may initiate a timer that counts a time period in which the authorization of the object must be received, else the processor may determine that the object is indeed unauthorized. In some implementations, the processor may require an authorization code together with the authorization (such as a password, a personal identification number (PIN), or another such authorization code) to verify the received authorization.

In determination block 316, the processor may determine whether the processor receives authorization of the object.

In response to determining that the processor has received authorization of the object (i.e., determination block 316="Yes"), the processor may store information about the authorized object in block 312. The processor may then receive UAV sensor data in block 302.

In response to determining that the processor has not received authorization of the object (i.e., determination block 316="No"), the processor may determine an action to perform in block 318. In some implementations, the processor may determine one or more actions to perform based on the received sensor data. In some implementations, based on the sensor data, the processor may determine an element or aspect of the unauthorized object, and may determine an action to perform based on the determined element or aspect. For example, the processor may determine that the unauthorized object includes an explosive chemical or compound, radiological material, toxic chemical, biohazardous material, or other hazardous materials. As another example, the processor may determine that the unauthorized object includes illegal or contraband goods. As another example, processor may determine that the unauthorized object include stolen goods.

For example, the processor may generate a visual, audible, tactile, etc. alert. In some implementations, the alert may be presented inside and/or outside the UAV. In some implementations, the processor may stop or prevent travel of the UAV. For example, the processor may land an aerial UAV, navigate an automotive UAV to the side of a road, or throttle down a watercraft UAV. In some implementations, the processor may reject the object, such as by preventing travel until the object is removed, or by presenting an alarm until the object is removed. In some implementations, the processor may send a message to the communication network, or to the wireless communication device, for example, to notify law enforcement, a fire department, or other authorities.

In some implementations, the processor may block or prevent further access to the object to secure the object to the UAV. For example, the processor may actuate a lock to a trunk or other cargo area, or prevent the release of a cargo holder, carrier, trailer hitch, etc., until a release code is provided. In some implementations, the processor may alter a path of the UAV. For example, the processor may navigate the UAV to the nearest police or other law enforcement location, to the closest fire station, or similar location.

In some implementations, the processor may broadcast warning related to the unauthorized object. For example, the processor may provide a visual and/or audible warning external to the UAV indicating the nature of the unauthorized object (for example that the unauthorized object is stolen, contraband, radioactive, etc.). As another example, the processor may transmit the warning to the communication network and/or the mobile communication device.

In block 320, the processor may perform the determined action. In some embodiments, the processor may perform two or more actions, without limitation. Then, the processor may again receive UAV sensor data in block 302.

Figure 4:
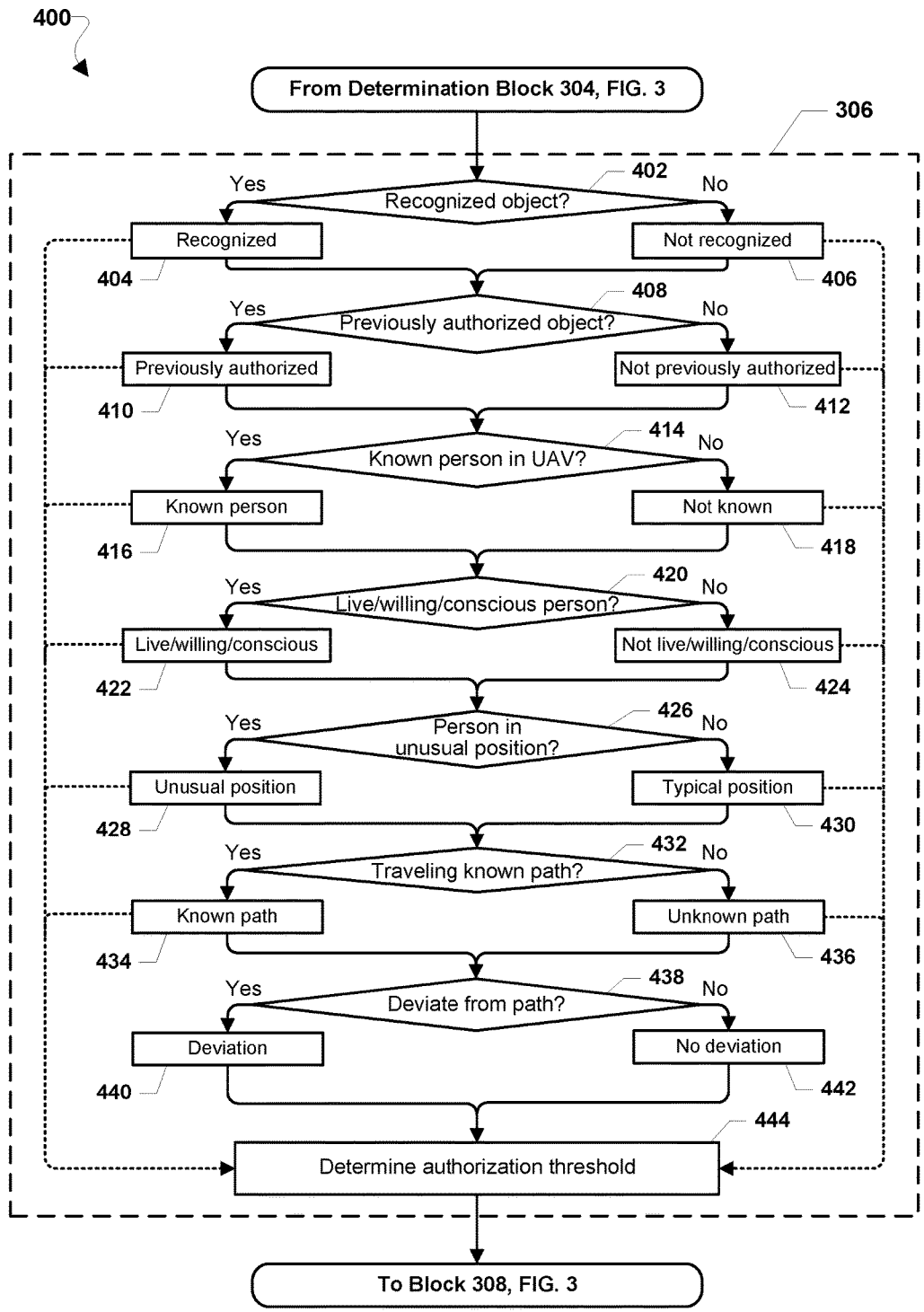
FIG. 4 is a process flow diagram illustrating an implementation method of providing security for a UAV.

FIG. 4 illustrates a method 400 of providing security for a UAV according to some implementations. The method 400 illustrates an example of operations that may be performed in block 306 of the method 300 as described with reference to FIG. 3 according to some implementations. With reference to FIGS. 1-4, the method 400 may be implemented by a UAV (e.g., the UAV 100), such as under the control of a processor (e.g., the processor 204) of the UAV. The order of operations performed in blocks 402-442 is merely illustrative, and the operations of blocks 402-442 may be performed in any order in various implementations.

As described above with regard to the method 300 (FIG. 3), in response to determining that the processor detects an object in contact with the UAV (i.e., determination block 304="Yes"), the processor may determine an authorization threshold in block 306. In various implementations, the processor may determine the authorization threshold based on the UAV sensor data. In determining the authorization threshold based on the UAV sensor data, the processor may perform one or more determinations about the sensor data that may indicate information about the object and/or people in or on the UAV that may enable the processor to characterize the sensor data according to variety of criteria. In various embodiments, the processor may use the characterize sensor data to determine the authorization threshold. Some examples of such determination operations are illustrated in the method 400. In various implementations, the processor may perform one or more of operations of blocks 402-442 to make one or more determinations about the UAV sensor data. In some embodiments, the result of one or more of the determinations in blocks 402-442 may be sufficiently definitive that the processor may proceed from a result to determine the authorization threshold in block 444.

For example, the processor may determine whether the object is recognized in determination block 402. In some implementations, the processor may determine whether the object is a recognized object, such as an object that the processor has previously detected. In some implementations, the processor may determine whether the object previously has been in contact with the UAV. For example, the processor may recognize the object as a purse, briefcase, a book bag, a golf bag, athletic equipment, or another object that has previously been in contact with the UAV. The processor may recognize the object based on sensor data from one or more sensors of the UAV (e.g., the sensors 102-140 and 218). The processor may also recognize the object based on a comparison of the data from the one or more sensors with a data structure stored in a memory of the UAV (e.g., the memory 206). For example, the data structure may include an identification of a previously detected object and sensor data associated with the previously detected object. The data structure may also include a pattern of sensor data that may enable the processor to recognize an object. Thus, in some implementations, the processor may determine that an object is a recognized object because the processor has previously detected the object and/or because the processor is able to identify the object based on sensor data from one or more sensors of the UAV.

In response to determining that the object is recognized (i.e., determination block 402="Yes"), the processor may generate an indication that the object is recognized in block 404. In some implementations, the processor may also generate information identifying the object. In some implementations and/or cases, the processor may determine that the recognition of the object is sufficiently close or strong (e.g., a percentage match or metric relating the degree of matching) that the authorization threshold may be determined in block 444 on the basis of the object recognition alone.

For example, if the processor determines that the object matches a commonly detected object (e.g., a book bag, a purse, briefcase, etc.) The authorization threshold may be determined in block 444 as a relatively low threshold that is satisfied by the recognized object. As another example, the processor may determine that the object is recognized, and that the object is forbidden, illegal, contraband, hazardous, or similarly undesirable. The authorization threshold may then be determined in block 444 as a relatively high threshold that is not satisfied by the recognized object.

In response to determining that the object is not recognized (i.e., determination block 402="No"), the processor may generate an indication that the object is not recognized in block 406. In some implementations and/or cases, the processor may determine that the lack of recognition is sufficient (i.e., is sufficiently different from a known object) that the processor may determine a relatively high authorization threshold in block 444 without further evaluations. In some implementations, the processor may use a determination that the object is recognized as a factor that may lower the authorization threshold. In some implementations, the processor may use a determination that the object is not recognized as a factor that may raise the authorization threshold.

In determination block 408, the processor may determine whether the object was previously authorized. For example, the processor may determine whether the object is not merely recognized but is also associated with a previous authorization. In some implementations, the processor may determine a degree of any previous authorizations. For example, the processor may determine a timing of the previous authorization (e.g., within a previous day, week, month, year, etc.). As another example, the processor may determine a number and/or frequency of previous authorizations, if any. As another example, the processor may determine whether one or more previous authorizations were provided by a known or authorized person (e.g., an owner or frequent authorized user of the UAV).

In response to determining that the object was previously authorized (i.e., determination block 408="Yes"), the processor may generate an indication that the object is previously authorized in block 410. In some implementations and/or cases, the processor may determine that the previous authorization is, for example, sufficiently recent, sufficiently frequent, sufficiently numerous, or was provided by an unauthorized person, that the authorization threshold may be determined in block 444 on the basis of the previous authorization alone.

In response to determining that the object was not previously authorized (i.e., determination block 408="No"), the processor may generate an appropriate indication in block 412. In some implementations and/or cases, the processor may determine that the lack of previous authorization is sufficient that the authorization threshold may be determined in block 444 based on the lack of previous authorization alone. In some implementations, the processor may use a determination that the object was previously authorized as a factor that may lower the authorization threshold. In some implementations, the processor may use a determination that the object was not previously authorized as a factor that may raise the authorization threshold.

In determination block 414, the processor may determine whether a person in the UAV is known. For example, the processor may determine whether the person is an authorized driver or passenger of the UAV, an owner of the UAV, a family member, a frequent guest, or a person who has otherwise been made known to the processor. In some implementations, the processor may determine whether the person in the UAV is known using sensor data and performing, for example, biometric recognition such as facial recognition, fingerprint recognition, iris or retina recognition, or similar biometric authentication. In some implementations, the processor may recognize an electronic token, tag, or another device that indicates to the processor a known person.

In response to determining that the person in the UAV is known (i.e., determination block 414="Yes"), the processor may generate an indication that the person is known in block 416. In some implementations, the known person may be someone permitted in the UAV. In some implementations, the known person may be someone forbidden from being in the UAV. In some implementations and/or cases, the processor may determine that the presence of the known person in the UAV is sufficient that the authorization threshold may be determined in block 444 based on the presence of the known person alone.

In response to determining that the person in the UAV is not known (i.e., determination block 414="No"), the processor may generate an appropriate indication in block 418. In some implementations, the absence of the known person may include the presence of an unknown person. In some implementations, the absence of the known person may include no person being detected in the UAV. In some implementations and/or cases, the processor may determine that the presence of an unknown person in the UAV is not known is sufficient that the authorization threshold may be determined block 444 based on such determination alone. In some implementations, the processor may use a determination that the person in the UAV is known as a factor that may lower the authorization threshold. In some implementations, the processor may use a determination that the person in the UAV is not known as a factor that may raise the authorization threshold.

In determination block 420, the processor may determine whether a person present in the UAV is alive, willing, and/or conscious. The processor may use a variety of sensor data to determine behaviors and/or data that may tend to indicate whether a person is alive, willing, and/or conscious. For example, the processor may measure seat pressure over time to detect, for example, a shifting in a seat position (or lack thereof). As another example, the processor may use camera data for face recognition and paste action recognition, such as eye blinks, changes in expression, and the like. As another example, the processor may 3-D camera data to distinguish between an actual person and a photograph or other two-dimensional representation of a person. As another example, the processor may use camera data to analyze body poses over time, which may indicate freedom (or lack of freedom) of movement. As another example, the processor may measure skin conductance, body motion, and/or heart rate estimation to detect a person's emotional state. As another example, the processor may use microphone data for speech detection, speech pattern detection, for stress analysis, and the like.

In response to determining that a person is alive, willing, and conscious (i.e., determination block 420="Yes"), the processor may generate an indication that the person is alive, willing, and conscious in block 422. In some implementations and/or cases, the processor may determine that the determination of the alive, willing, and conscious person is sufficient that the authorization threshold may be determined in block 444 based on the presence of the alive, willing, and conscious person alone, particularly in combination with other determinations that have been made.

In response to determining that the person is not one of alive, willing, or conscious (i.e., determination block 420="No"), the processor may generate an appropriate indication in block 424. In some implementations, the indication that a person in the UAV is one or more of not alive, not willing, or not conscious is be sufficient that the authorization threshold may be determined block 444 based on such determination alone, particularly in combination with other determinations that have been made. In some implementations, the processor may use a determination that the person is alive, willing, and conscious as a factor that may lower the authorization threshold. In some implementations, the processor may use a determination that the person is not one of alive, willing, or conscious as a factor that may raise the authorization threshold.

In determination block 426, the processor may determine whether a person is in an unusual position. In some implementations, the unusual position may include a person not a typical posture for driving or riding in the UAV, such as prone, lying across seats, slumped over, and the like. In some implementations, the unusual position may include a person being in an unusual location of the UAV, for example in the trunk or another cargo area.

In response to determining that a person is in an unusual position (i.e., determination block 426="Yes"), the processor may generate an indication that the person is in an unusual position in block 428. In some implementations, the indication that the person is in an unusual position may be sufficient that the authorization threshold may be determined block 444 based on such determination alone, particularly in combination with other determinations that have been made.

In response to determining that a person is not in an unusual position (i.e., determination block 426="No"), the processor may generate an indication that the person is in a typical position (i.e., not in an unusual position) in block 430. In some implementations, the indication that the person is not in an unusual position may be sufficient that the authorization threshold may be determined block 444 based on such determination alone, particularly in combination with other determinations that have been made. In some implementations, the processor may use a determination that the person is in an unusual position as a factor that may lower the authorization threshold. In some implementations, the processor may use a determination that the person is not in an unusual position as a factor that may raise the authorization threshold.

In determination block 432, the processor may determine whether the UAV is traveling a known path. In some implementations, the processor may continuously authenticate the path traveled by the UAV. For example, the processor may use positioning system, accelerometer data, odometer data, or other sensor inputs to continuously authenticate a path traveled by the UAV. The path may include a destination that is input to the processor, or a continuously updated route toward a defined location. The path may also include a known or commonly traveled path, such to a home, a work location, a school location, common errands, and the like.

In response to determining that the UAV is traveling a known path (i.e., determination block 432="Yes"), the processor may generate an indication that the UAV is traveling the known path in block 434. In some implementations, the indication that the UAV is traveling in half may be sufficient that the authorization threshold may be determined block 444 based on such determination alone.

In response to determining that the UAV is not traveling a known path (i.e., determination block 432="No"), the processor may generate an indication that the UAV is not traveling a known path (e.g., an unknown path) in block 436. In some implementation, an unknown path may include a path that the UAV has not previously traveled. In some implementations, the unknown path may include a path that is not an authorized or pre-approved path (e.g., from among a set of authorized or pre-approved paths). In some implementations, a known path may include a path for which the UAV is authorized (e.g., based on a previous and/or contemporaneous input). In some implementations, a known path may include a path that the UAV is prohibited from traveling. In some implementations, the indication that the UAV is not traveling a known path (i.e., the UAV is traveling an unknown path) may be sufficient that the authorization threshold may be determined block 444 based on such determination alone, particularly in combination with other determinations that have been made available.

In some implementations, the processor may use a determination that the UAV is traveling a known path as a factor that may lower the authorization threshold. In some implementations, the processor may use a determination that the UAV is not traveling a known path as a factor that may raise the authorization threshold. In some implementations, the factor may also depend on the degree of the determination. For example, the processor may increase the authorization threshold to a first extent based on a determination that the UAV path has not been previously traveled, and the processor may increase the authorization threshold to a greater second extent based on a determination that the UAV path is not a pre-approved path. Further, the processor may increase the authorization threshold to a yet greater third extent based on a determination that the UAV path is a prohibited path. As another example, the processor may decrease the authorization threshold by a first extent based on a determination that the UAV path is known, and may decrease the authorization threshold by a second greater extent based on the determination that the UAV path is known and authorized for the UAV.

In determination block 438, the processor may determine whether the UAV deviates from a path. In some implementations, the processor may determine whether the UAV deviates from a selected path or path that is input by user. In some implementations, the processor may determine whether the UAV deviates from a known or commonly traveled path (e.g. home, work, school, known shops, etc.). In some cases, the UAV may deviate from a path, for example, to accommodate a detour, or to avoid traffic congestion or an accident. In some cases, the UAV may deviate from a path because the UAV has been compromised in some way (such as being stolen, or be subject to a software hack). In some implementations, the processor may determine whether the UAV deviates from an unknown path (e.g., a path that has never been traveled before, and that the UAV also deviates from). In some embodiments, determining whether the UAV deviates from the path may include determining whether a deviation is authorized (e.g., to avoid traffic congestion) or unauthorized (e.g., not approved by a passenger).

In some implementations, the processor may use a determination that the UAV does not deviate from the path as a factor that may lower the authorization threshold. In some implementations, the processor may use a determination that the UAV deviates from the path as a factor that may raise the authorization threshold. In some implementations, the factor may also depend on the degree of the determination. For example, the device processor may increase the authorization threshold to a first extent based on a determination that the UAV deviates from the path, e.g. to accommodate a detour to avoid traffic congestion, and may increase the authorization threshold to a second greater extent based on a determination that the UAV deviates from the path, e.g. because the UAV has been compromised. In response to determining that the UAV has deviated from the path (i.e., determination block 438="Yes"), the processor may generate an indication that the UAV has deviated from the path in block 440. In some implementations, the indication that the UAV has deviated from the path may be sufficient that the authorization threshold may be determined block 444 based on such determination alone.

In response to determining that the UAV has not deviated from the path (i.e., determination block 438="No"), the processor may generate an appropriate indication in block 442. In some implementations, the processor may determine that the deviation from the path meets a threshold deviation from a known or commonly traveled path. In some implementations, the indication that the UAV has deviated from the path may be sufficient that the authorization threshold may be determined in block 444 based on such determination alone, particularly in combination with other determinations that have been made available.

In block 444, based on one or more determinations based on the received sensor data, the processor of the UAV may determine the authorization threshold. The determined authorization threshold may then be applied in block 308 of the method 300 as described with reference to FIG. 3.

Thus, various embodiments and implementations may improve the operation of a UAV by providing security to the UAV related to the detection and evaluation of objects that may be placed in or on the UAV. Various implementations improve the operation of the UAV by determining whether an object in contact with the UAV is authorized. Various implementations also improve the operation of the UAV by dynamically determining an authorization threshold for an object in contact with the UAV based on real-time UAV sensor data.

Various implementations illustrated and described are provided merely as examples to illustrate various features of the claims. However, features shown and described with respect to any given implementation are not necessarily limited to the associated implementation and may be used or combined with other implementations that are shown and described. Further, the claims are not intended to be limited by any one example implementation. For example, one or more of the operations of the method 300 may be substituted or combined with one or more operations of the method 400 and vice versa.

The foregoing method descriptions and the process flow diagrams are provided merely as illustrative examples and are not intended to require or imply that the blocks of various implementations must be performed in the order presented. As will be appreciated by one of skill in the art the order of blocks in the foregoing implementations may be performed in any order. Words such as "thereafter," "then," "next," etc. are not intended to limit the order of the blocks; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm blocks described in connection with the implementations disclosed herein may be implemented as electronic hardware, computer software, or combinations of both. To clearly illustrate this interchangeability of hardware and software, various illustrative components, blocks, modules, circuits, and blocks have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of various implementations.

The hardware used to implement the various illustrative logics, logical blocks, modules, and circuits described in connection with the implementations disclosed herein may be implemented or performed with a general-purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of communication devices, e.g., a combination of a DSP and a microprocessor, a plurality of microprocessors, one or more microprocessors in conjunction with a DSP core, or any other such configuration. Alternatively, some blocks or methods may be performed by circuitry that is specific to a given function.

In various implementations, the functions described may be implemented in hardware, software, firmware, or any combination thereof. If implemented in software, the functions may be stored as one or more instructions or code on a non-transitory computer-readable medium or non-transitory processor-readable medium. The operations of a method or algorithm disclosed herein may be embodied in a processor-executable software module, which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed implementations is provided to enable any person skilled in the art to make or use the present implementations. Various modifications to these implementations will be readily apparent to those skilled in the art, and the generic principles defined herein may be applied to other implementations without departing from the scope of the implementations. Thus, various implementations are not intended to be limited to the implementations shown herein but are to be accorded the widest scope consistent with the following claims and the principles and novel features disclosed herein.

What is claimed is:

1. A method of providing security for an unmanned autonomous vehicle (UAV), comprising:
   receiving real-time sensor data from a plurality of UAV sensors about at least one physical characteristic of a cargo object in contact with the UAV;
   determining an authorization threshold for the cargo object based on the received real-time sensor data, wherein the authorization threshold is dynamically determined based on the at least one physical characteristic of the cargo object; and
   determining whether the cargo object is authorized based on the received real-time sensor data and the determined authorization threshold.

2. The method of claim 1, wherein determining the authorization threshold for the cargo object based on the received real-time sensor data comprises:
   determining whether the cargo object is a recognized object; and
   determining the authorization threshold for the cargo object based on whether the cargo object is a recognized object.

3. The method of claim 1, wherein determining the authorization threshold for the cargo object based on the received real-time sensor data comprises:
   determining whether the cargo object is a previously authorized object; and
   determining the authorization threshold for the cargo object based on whether the cargo object is a previously authorized object.

4. The method of claim 1, wherein determining the authorization threshold for the cargo object based on the received real-time sensor data comprises:
   determining whether a person in the UAV is a known person; and
   determining the authorization threshold for the cargo object based on whether the person in the UAV is a known person.

5. The method of claim 1, wherein determining the authorization threshold for the cargo object based on the received real-time sensor data comprises:
   determining whether a person in the UAV is an alive, willing, and conscious person; and
   determining the authorization threshold for the cargo object based on whether the person in the UAV is an alive, willing, and conscious person.

6. The method of claim 1, wherein determining the authorization threshold for the cargo object based on the received real-time sensor data comprises:
   determining whether a person in the UAV is in an unusual position; and
   determining the authorization threshold for the cargo object based on whether the person in the UAV is in an unusual position.

7. The method of claim 1, wherein determining the authorization threshold for the cargo object based on the received real-time sensor data comprises:
   determining whether the UAV is traveling a known path; and
   determining the authorization threshold for the cargo object based on whether the UAV is traveling the known path.

8. The method of claim 1, wherein determining the authorization threshold for the cargo object based on the received real-time sensor data comprises:
   determining whether the UAV deviates from a path; and
   determining the authorization threshold for the cargo object based on whether the UAV deviates from the path.

9. The method of claim 1, further comprising:
   storing information about the cargo object in response to determining that the cargo object is authorized.

10. The method of claim 1, further comprising:
    generating an indication that the cargo object is unauthorized in response to determining that the cargo object is not authorized.

11. The method of claim 1, further comprising:
    determining an action to perform when the cargo object is not authorized; and
    performing the determined action.

12. The method of claim 11, further comprising:
    determining whether an authorization of an unauthorized cargo object is received; and
    determining the action to perform in response to determining that the authorization of the unauthorized cargo object is not received.

13. An unmanned autonomous vehicle (UAV), comprising:
    a plurality of sensors; and
    a processor coupled to the plurality of sensors and configured with processor-executable instructions to perform operations comprising:
       receiving real-time sensor data from the plurality of sensors about at least one physical characteristic of a cargo object in contact with the UAV;
       determining an authorization threshold for the cargo object based on the received real-time sensor data, wherein the authorization threshold is dynamically determined based on the at least one physical characteristic of the cargo object; and
determining whether the cargo object is authorized based on the received real-time sensor data and the determined authorization threshold.

14. The UAV of claim 13, wherein the processor is configured with processor-executable instructions to perform operations such that determining the authorization threshold for the cargo object based on the received real-time sensor data comprises:
determining whether the cargo object is a recognized object; and
determining the authorization threshold for the cargo object based on whether the cargo object is a recognized object.

15. The UAV of claim 13, wherein the processor is configured with processor-executable instructions to perform operations such that determining the authorization threshold based on the received real-time sensor data comprises:
determining whether the cargo object is a previously authorized object; and
determining the authorization threshold based on whether the cargo object is a previously authorized object.

16. The UAV of claim 13, wherein the processor is configured with processor-executable instructions to perform operations such that determining the authorization threshold for the cargo object based on the received real-time sensor data comprises:
determining whether a person in the UAV is a known person; and
determining the authorization threshold for the cargo object based on whether the person in the UAV is a known person.

17. The UAV of claim 13, wherein the processor is configured with processor-executable instructions to perform operations such that determining the authorization threshold for the cargo object based on the received real-time sensor data comprises:
determining whether a person in the UAV is an alive, willing, and conscious person; and
determining the authorization threshold for the cargo object based on whether the person in the UAV is an alive, willing, and conscious person.

18. The UAV of claim 13, wherein the processor is configured with processor-executable instructions to perform operations such that determining the authorization threshold for the cargo object based on the received real-time sensor data comprises:
determining whether a person in the UAV is in an unusual position; and
determining the authorization threshold for the cargo object based on whether the person in the UAV is in an unusual position.

19. The UAV of claim 13, wherein the processor is configured with processor-executable instructions to perform operations such that determining the authorization threshold for the cargo object based on the received real-time sensor data comprises:
determining whether the UAV is traveling a known path; and
determining the authorization threshold for the cargo object based on whether the UAV is traveling the known path.

20. The UAV of claim 13, wherein the processor is configured with processor-executable instructions to perform operations such that determining the authorization threshold for the cargo object based on the received real-time sensor data comprises:
determining whether the UAV deviates from a path; and
determining the authorization threshold for the cargo object based on whether the UAV deviates from the path.

21. The UAV of claim 13, wherein the processor is configured with processor-executable instructions to perform operations further comprising:
storing information about the cargo object in response to determining that the cargo object is authorized.

22. The UAV of claim 13, wherein the processor is configured with processor-executable instructions to perform operations further comprising:
generating an indication that the cargo object is unauthorized in response to determining that the cargo object is not authorized.

23. The UAV of claim 13, wherein the processor is configured with processor-executable instructions to perform operations further comprising:
determining an action to perform when the cargo object is not authorized; and
performing the determined action.

24. The UAV of claim 23, wherein the processor is configured with processor-executable instructions to perform operations further comprising:
determining whether an authorization of an unauthorized cargo object is received; and
determining the action to perform in response to determining that the authorization of the unauthorized cargo object is not received.

25. A non-transitory processor-readable storage medium having stored thereon processor-executable instructions configured to cause a processor of an unmanned autonomous vehicle (UAV) to perform operations for providing security comprising:
receiving real-time sensor data from a plurality of UAV sensors about at least one physical characteristic of a cargo object in contact with the UAV;
determining an authorization threshold for the cargo object based on the received real-time sensor data, wherein the authorization threshold is dynamically determined based on the at least one physical characteristic of the cargo object; and
determining whether the cargo object is authorized based on the received real-time sensor data and the determined authorization threshold.

26. The non-transitory processor-readable storage medium of claim 25, wherein the stored processor-executable instructions are configured to cause the processor of the UAV to perform operations such that determining the authorization threshold for the cargo object based on the received real-time sensor data comprises:
determining whether the cargo object is a recognized object; and
determining the authorization threshold for the cargo object based on whether the cargo object is a recognized object.

27. The non-transitory processor-readable storage medium of claim 25, wherein the stored processor-executable instructions are configured to cause the processor of the UAV to perform operations such that determining the authorization threshold for the cargo object based on the received real-time sensor data comprises:
determining whether the cargo object is a previously authorized object; and determining the authorization threshold for the cargo object based on whether the object is a previously authorized object.

28. The non-transitory processor-readable storage medium of claim 25, wherein the stored processor-executable instructions are configured to cause the processor of the UAV to perform operations such that determining the authorization threshold for the cargo object based on the received real-time sensor data comprises:
   determining whether a person in the UAV is a known person; and
   determining the authorization threshold for the cargo object based on whether the person in the UAV is a known person.

29. The non-transitory processor-readable storage medium of claim 25, wherein the stored processor-executable instructions are configured to cause the processor of the UAV to perform operations such that determining the authorization threshold for the cargo object based on the received real-time sensor data comprises:
   determining whether a person in the UAV is an alive, willing, and conscious person; and
   determining the authorization threshold for the cargo object based on whether the person in the UAV is an alive, willing, and conscious person.

30. An unmanned autonomous vehicle (UAV), comprising:
   means for receiving real-time sensor data from a plurality of UAV sensors about at least one physical characteristic of a cargo object in contact with the UAV;
   means for determining an authorization threshold for the cargo object based on received real-time sensor data, wherein the authorization threshold is dynamically determined based on the at least one physical characteristic of the cargo object; and
   means for determining whether the cargo object is authorized based on the received real-time sensor data and the determined authorization threshold.

* * * * *